US006558331B1

(12) United States Patent
Davidsen et al.

(10) Patent No.: US 6,558,331 B1
(45) Date of Patent: May 6, 2003

(54) APPARATUS AND METHOD FOR HARMONIC IMAGING USING AN ARRAY TRANSDUCER OPERATED IN THE $K_{31}$ MODE

(75) Inventors: Richard E. Davidsen, Everett, WA (US); Loriann R. Davidsen, Everett, WA (US); David N. Roundhill, Woodinville, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/158,525

(22) Filed: May 29, 2002

(51) Int. Cl.[7] ................................................ A61B 8/00

(52) U.S. Cl. ...................... 600/459; 310/322; 310/334; 29/25.35

(58) Field of Search ......................... 600/459; 310/334, 310/322, 357, 358, 328, 335, 336, 337; 29/25.35; 73/626

(56) References Cited

U.S. PATENT DOCUMENTS

| | | | | | |
|---|---|---|---|---|---|
| 4,914,565 | A | | 4/1990 | Schnoeller et al. | |
| 5,187,403 | A | | 2/1993 | Larson, III | |
| 5,410,205 | A | | 4/1995 | Gururaja | |
| 5,415,175 | A | * | 5/1995 | Hanafy et al. | 600/459 |
| 5,548,564 | A | | 8/1996 | Smith | |
| 5,553,035 | A | | 9/1996 | Seyed-Bolorforosh et al. | |
| 5,625,149 | A | | 4/1997 | Gururaja et al. | |
| 5,825,117 | A | | 10/1998 | Ossmann et al. | |
| 5,957,851 | A | | 9/1999 | Hossack | |
| 6,014,897 | A | | 1/2000 | Mo | |
| 6,206,833 | B1 | | 3/2001 | Christopher | |
| 6,225,728 | B1 | * | 5/2001 | Gururaja | 310/334 |
| 6,288,477 | B1 | * | 9/2001 | Gilmore et al. | 310/334 |
| 6,457,365 | B1 | * | 10/2002 | Stephens et al. | 73/626 |
| 6,467,140 | B2 | * | 10/2002 | Gururaja | 29/25.35 |

OTHER PUBLICATIONS

Bolorforosh, M.S.S., "Dual Frequency Piezoelectric Transducer for Medical Applications,"SPIE vol. 1773, (1992), pp. 131 et seq.

Mills et al., "Combining Multi–Layers and Composites to Increase SNR for Medical Ultrasound Transducers," 1996 IEEE Ultrasonics Symposium, pp. 1509–1512.

* cited by examiner

*Primary Examiner*—Francis J. Jaworski
*Assistant Examiner*—Ruby Jain
(74) *Attorney, Agent, or Firm*—W. Brinton Yorks, Jr.

(57) ABSTRACT

A method and apparatus are described for harmonic imaging using a transducer operated in the $k_{31}$ mode. In one embodiment, the invention includes a transducer operative in a $k_{31}$ mode, a transmitter for transmitting first signals to the transducer assembly, and a receiver for processing second signals received by the transducer assembly at a harmonic of the frequency of the first signals. In another embodiment, a method of operating an ultrasound system includes emitting first signals in a first frequency range from a transducer operating in the $k_{31}$ mode, projecting the signals into a body, and detecting second signals confined to a second frequency range.

20 Claims, 3 Drawing Sheets

APPARATUS AND METHOD FOR HARMONIC IMAGING USING AN ARRAY TRANSDUCER OPERATED IN THE $K_{31}$ MODE

TECHNICAL FIELD

This invention relates generally to ultrasound diagnostic imaging systems, and more particularly, to an apparatus and method for harmonic imaging using such systems.

BACKGROUND OF THE INVENTION

Ultrasonic diagnostic imaging systems are in widespread use for performing ultrasonic imaging and measurements. Diagnostic images are obtained from these systems by placing a transducer assembly against the skin of a patient, and actuating one or more piezoelectric elements located within the transducer assembly to transmit ultrasonic energy through the skin and into the body of the patient. In response, ultrasonic reflections are returned from the interior structure of the body, which are converted into electrical signals by the piezoelectric elements in the transducer assembly.

Since the fluids and tissues comprising the body of the patient have a significant non-linear acoustic response when exposed to ultrasound energy, harmonic reflections are often generated within the body at one or more frequencies that are harmonically related to a fundamental transmit frequency. Harmonic imaging systems have thus been developed that emit ultrasonic energy at a selected frequency, and receive reflected or transmitted ultrasonic energy at one or more harmonic frequencies of the selected transmission frequency.

Currently, conventional broad-band transducer assemblies are used in harmonic imaging systems that are generally configured to be operable within a predetermined bandwidth that includes a range of frequencies centered about a fundamental transmit frequency. As a consequence, the transducer assembly generally exhibits favorable sensitivity at frequencies that are close to the fundamental frequency, but exhibits generally less sensitivity to frequencies near the edges of a prescribed bandwidth. Since harmonic reflections of interest often occur at frequencies near the edge of the transducer bandwidth, the sensitivity of the transducer assembly to these frequencies is often substantially reduced.

Prior attempts to achieve wide bandwidth transducer assemblies for use in harmonic imaging systems have followed at least two general approaches. One approach is to optimize the design of passive components used in the assembly, including multiple matching layers and/or backing layers to achieve broader frequency response. Transducer assemblies following this approach generally have the same frequency response when transmitting and receiving, with the ultrasound system being used to select a desired frequency response by altering the transmit waveform and/or altering the receive filter response. Since the number of passive components which can be assembled is usually very limited, this approach generally achieves only limited bandwidth improvement without compromising other performance parameters such as sensitivity.

A second approach is to optimize the design of the active components of the transducer assembly, which are generally comprised of a piezoelectric material. In one method, the piezoelectric layer material is formed with a varying thickness in a selected direction, so that the frequency response of the transducer element is broadened, as described in various publications (e.g., "Dual Frequency Piezoelectric Transducer for Medical Applications," M. S. S. Bolorforosh, SPIE Vol. 1733, (1992) at pp. 131 et seq.) and patents (e.g., U.S. Pat. No. 5,415,175 to Hanafy, et al.). In another method, transducer elements are fabricated with multiple layers of active transducer materials, and use a switching circuit to control the polarity of each layer or to control the signal applied to each layer, in order to generate different frequency response characteristics for the transducer elements during the transmit and receive modes. For example, U.S. Pat. No. 5,410,205 to Gururaja discloses a transducer stack consisting of two or more electrostrictive layers that may be selectively biased by applying a voltage to each layer so that the transducer transmits at one resonance frequency and receives at another resonance frequency. Further, U.S. Pat. No. 5,825,117 to Ossmann, et al. and U.S. Pat. No. 5,957,851 to Hossack also disclose transducer stacks consisting of two piezoelectric layers. Switching circuits are attached to each transducer element so that different frequency responses can be generated during the transmit and receive modes. A drawback of this approach is the requirement of additional electronic circuits associated with each transducer element to control the different modes, thus adding to the complexity of the transducer assembly.

It is therefore desirable to provide an ultrasound diagnostic imaging system that is optimized to permit the transmission of ultrasound energy at a fundamental frequency that also permits the detection of reflected ultrasound energy at harmonic frequencies with greater sensitivity than is currently obtainable from systems using conventional broad-band transducer assemblies. It is further desirable to provide a system that provides the foregoing advantages without the use of multiple transducer layers or switching elements to control the spectral response of the transducer assembly.

SUMMARY OF THE INVENTION

The invention is generally directed towards ultrasound diagnostic imaging systems, and more particularly, to an apparatus and method for harmonic imaging using such systems. In one aspect, the invention includes a transducer assembly including at least one layer formed from a piezoelectric material extending in a first direction and in a second direction that is perpendicular to the first direction and having electrodes positioned on opposing sides of the layer, the piezoelectric material being poled in the second direction, and an ultrasound processor operatively coupled to the electrodes, the processor transmitting first signals to the transducer assembly for generating ultrasonic waves, and receiving second signals from the transducer assembly corresponding to reflected portions of the ultrasonic waves, the second signals being harmonically related to the first signals. In another aspect, the invention includes a transducer assembly configured for operation in a $k_{31}$ mode, a transmitter for transmitting first signals to the transducer assembly, the first signals including a first frequency, and a receiver for processing second signals received by the transducer assembly, the second signals including a second frequency harmonically related to the first frequency. In still another aspect, the invention includes a method of operating an ultrasound imaging system that includes emitting first ultrasound signals from a transducer assembly operating in the $k_{31}$ mode, the first signals being confined to a first frequency range, projecting the first ultrasound signals into a body, and detecting second ultrasound signals corresponding to reflected portions of the first signals, the second signals being confined to a second frequency range different from the first frequency range.

DETAILED DESCRIPTION OF THE INVENTION

This invention relates generally to ultrasound diagnostic imaging systems, and more particularly, to an apparatus and method for harmonic imaging using such systems. Many of the specific details of certain embodiments of the invention are set forth in the following description and in FIGS. 1 through 4 to provide a thorough understanding of such embodiments. One skilled in the art will understand, however, that the present invention may be practiced without several of the details described in the following description. Moreover, in the description that follows, it is understood that the figures related to the various embodiments are not to be interpreted as conveying any specific or relative physical dimensions, and that specific or relative dimensions, if stated, are not to be considered limiting unless the claims expressly state otherwise.

Figure 1:
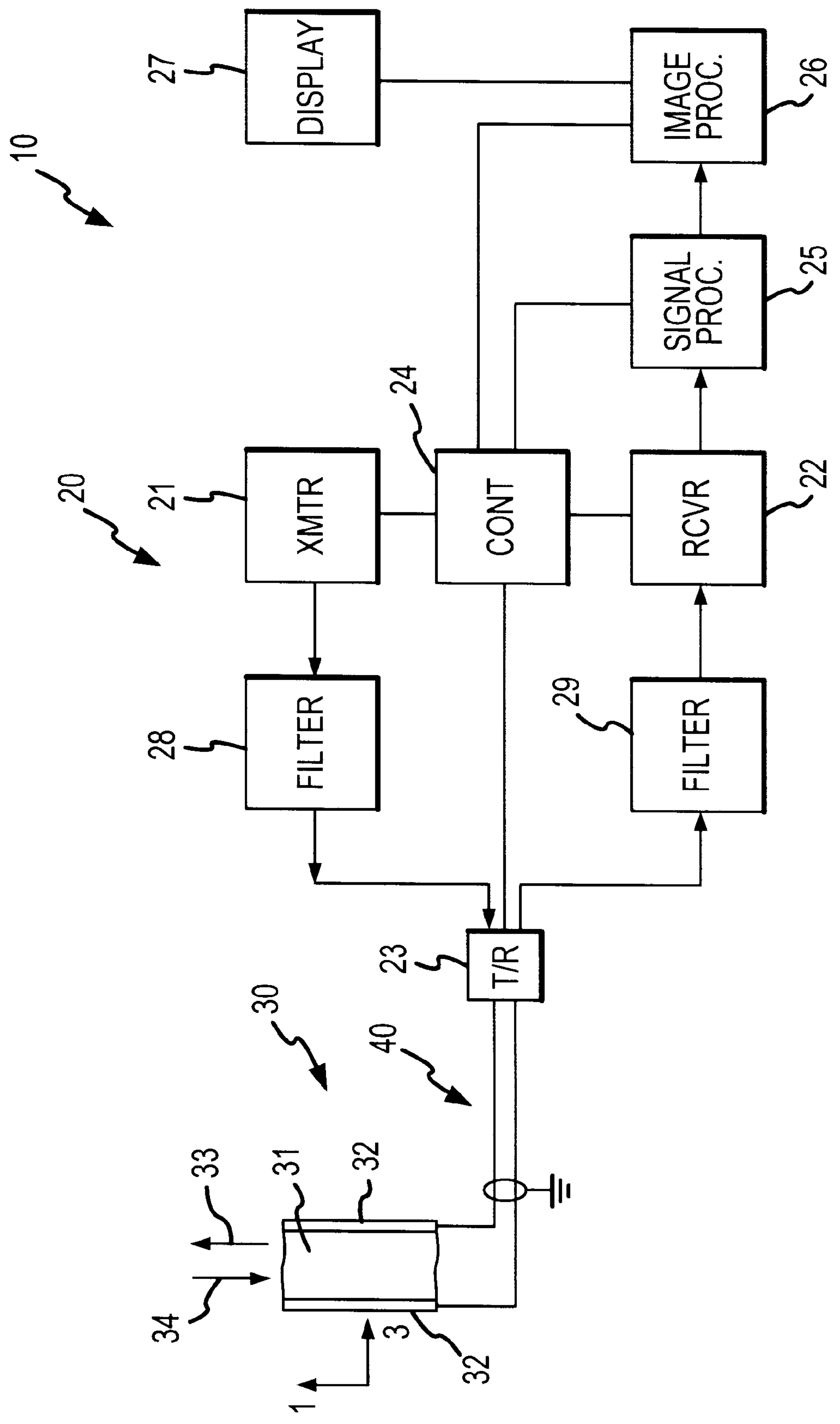
FIG. 1 is a functional block diagram of an ultrasound imaging system according to an embodiment of the invention.

FIG. 1 is a functional block diagram of an ultrasound imaging system 10 according to an embodiment of the invention. The system 10 includes an ultrasound processor 20 that is coupled to a transducer assembly 30 by a cable 40. The transducer assembly 30 will be described in greater detail below. The ultrasound processor 20 further includes a transmitter 21 that generates signals at ultrasonic frequencies for emission by the transducer assembly 30, and a receiver 22 to detect signals received by the transducer assembly 30. In order to isolate the transmitter 21 from the transducer assembly 30, a transmit/receive (T/R) switch 23 decouples the transmitter 21 from the transducer assembly 30 while the receiver 22 is detecting signals. The T/R switch 23 similarly decouples the receiver 22 from the transducer assembly 30 while the transmitter 21 is operatively emitting signals. A system controller 24 interacts with the transmitter 21, the receiver 22, and the T/R switch 23 to coordinate the operation of these components. The controller 24 similarly interacts with a signal processing unit 25 that receives and processes signals received by the receiver 22 and an image processing unit 26 that further processes signals received from the signal processor 25 to produce a visual image of an insonified region on a visual display 27.

Still referring to FIG. 1, signals generated by the transmitter 21 may be passed through a filter network 28 before the signals are transferred to the transducer assembly 30. The network 28 allows ultrasonic energy within a selected transmission frequency band to be transferred to the transducer assembly 30, while substantially attenuating the ultrasonic signals at other frequencies outside the band. The signals received from the transducer assembly 30 may similarly be filtered by a filter network 29 before the signals are detected by the receiver 22. The network 29 allows ultrasonic energy within a selected frequency reception band to be transferred to the receiver 22. The reception band and the transmission band are substantially spaced apart, so that frequency overlap generally does not occur between the two bands. In a particular embodiment, the filter 28 is configured to pass frequencies corresponding to approximately about a fundamental resonant frequency of the transducer assembly 30, while the filter 29 is configured to pass one or more frequencies that are harmonically related to the fundamental resonant frequency. The networks 28 and 29 may include devices capable of providing selective spectral filtering, such as passive filter networks of Gaussian, Bessel or Chebyshev design, although other designs may also be used.

The transducer assembly 30 will now be described in detail, with reference still to FIG. 1. The assembly 30 includes a piezoelectric transducer element 31 that is capable of emitting ultrasonic waves 33 when excited by signals generated by the transmitter 21, and receiving ultrasonic waves 34 and converting the waves 34 to electrical signals that may be detected by the receiver 22. The transducer assembly 30 further includes electrodes 32 coupled to the transducer element 31 on opposing sides. The piezoelectric transducer element 31 may have a dimension that extends in a longitudinal direction 1 that is at least about twice the dimension extending in a lateral direction 3. In one particular embodiment, the dimension extending in the direction 1 is approximately three times the dimension extending in the direction 3. The transducer element 31 is further poled in the lateral direction 3 to permit the stimulation of one or more thickness vibrational modes in the transducer element 31, which extend in the longitudinal direction 1. Since the transducer element 31 is poled and driven in the direction 3 and emits ultrasonic energy in the 1 direction, the operating mode for the transducer element 31 is described as the $k_{31}$ mode. In contrast, prior art transducers are poled and driven in the 3 direction, and emit ultrasonic energy in the 3 direction, so that the mode of operation is commonly referred to as the $k_{33}$ mode of operation. A $k_{31}$ poled transducer assembly is further described in U.S. Pat. No. 6,288,477 B1 to Gilmore, et at, which is incorporated herein by reference. Gilmore et al. compare and contrast the construction and operation of a $k_{31}$ transducer element (FIG. 2) with that of a conventional $k_{33}$ transducer element (FIG. 1). Although a single transducer assembly 30 is shown in FIG. 1, it is understood that more than one assembly may be present, and that the assemblies may be arranged in a linear array of elements and electrodes, or in various two dimensional arrays. Further, the assemblies may be joined and suitably oriented to form curved, or shaped arrays to improve the directional capabilities of the ultrasound imaging system.

A significant advantage of the $k_{31}$ mode of operation is that various thickness vibrational modes for the transducer assembly 30 are particularly responsive to stimulation by higher-order harmonics of the fundamental transmission frequency. For example, a thickness vibrational mode corresponding to a third harmonic frequency generally exhibits an amplitude with a magnitude that is approximately about the magnitude of a mode corresponding to the fundamental, when the transducer is operated in the $k_{31}$ mode. In comparison, a comparable thickness mode amplitude for a transducer operated in the $k_{33}$ mode would typically be significantly lower in magnitude when compared to the fundamental.

Figure 2:
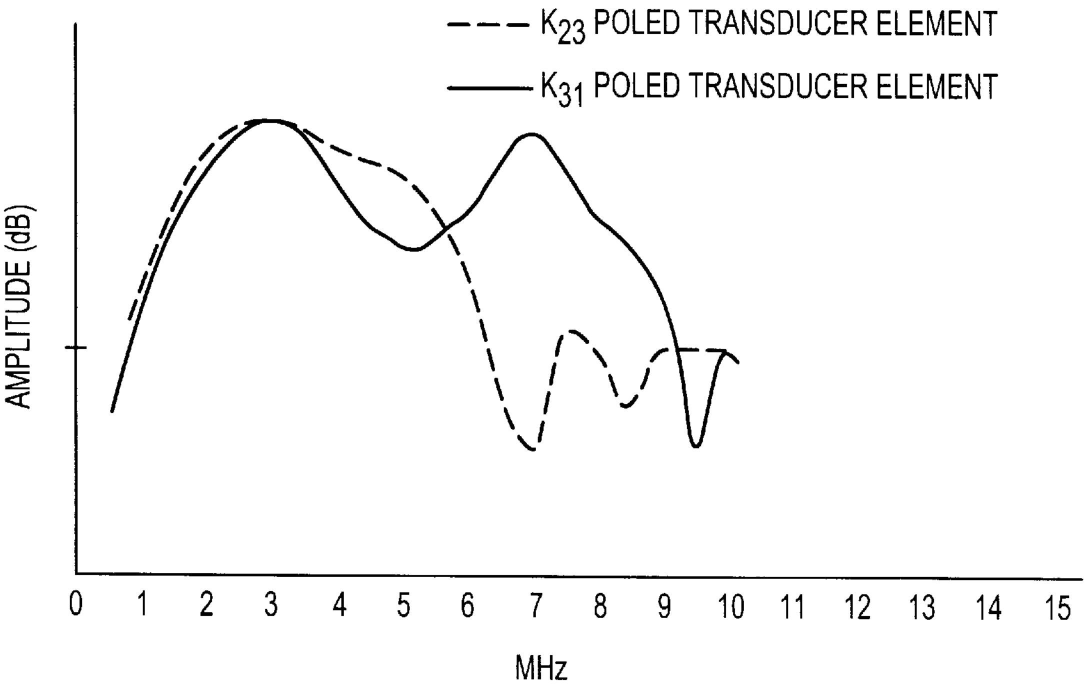
FIG. 2 is a graph comparing the response of a transducer assembly of the imaging system when operated in the $k_{31}$ and $k_{33}$ modes of operation.

FIG. 2 is a graph comparing the response of the transducer assembly 30 operating in the $k_{31}$ with a transducer operating in the $k_{33}$ mode of operation, which will be used to further describe the enhanced response of the $k_{31}$ mode of operation to higher order harmonics. In each instance, the transducer was exposed to ultrasonic energy emitted by an ultrasonic source at a frequency that approximately corresponds to a third harmonic frequency (in the present example, at approximately about 6.8 MHz) of a fundamental frequency (approximately 2.6 MHz). As shown therein, each transducer exhibits a fundamental resonance at approximately about 2.6 MHz when operated in either the $k_{33}$ mode or the $k_{31}$ mode of operation. When the assembly 30 in FIG. 1 is replaced by a transducer operating in the $k_{33}$ mode, little or no resonance at approximately 6.8 MHz is observed, indicating that the transducer exhibits relatively low sensitivity to stimulation at the third harmonic frequency. In contrast, when the assembly 30 is operated in the $k_{31}$ mode, a relatively strong resonance occurs at the third harmonic frequency (at approximately about 6.8 MHz), with the amplitude of the resonant mode being approximately on the order of the amplitude of the fundamental resonance (approximately 2.6 MHz). Operation of the transducer assembly 30 in the $k_{31}$ mode thus advantageously permits harmonic frequencies of the fundamental resonant mode to be detected with greater sensitivity than is obtainable when a transducer is operated in the $k_{33}$ mode, as shown in the bimodal response characteristic of FIG. 2.

Figure 3:
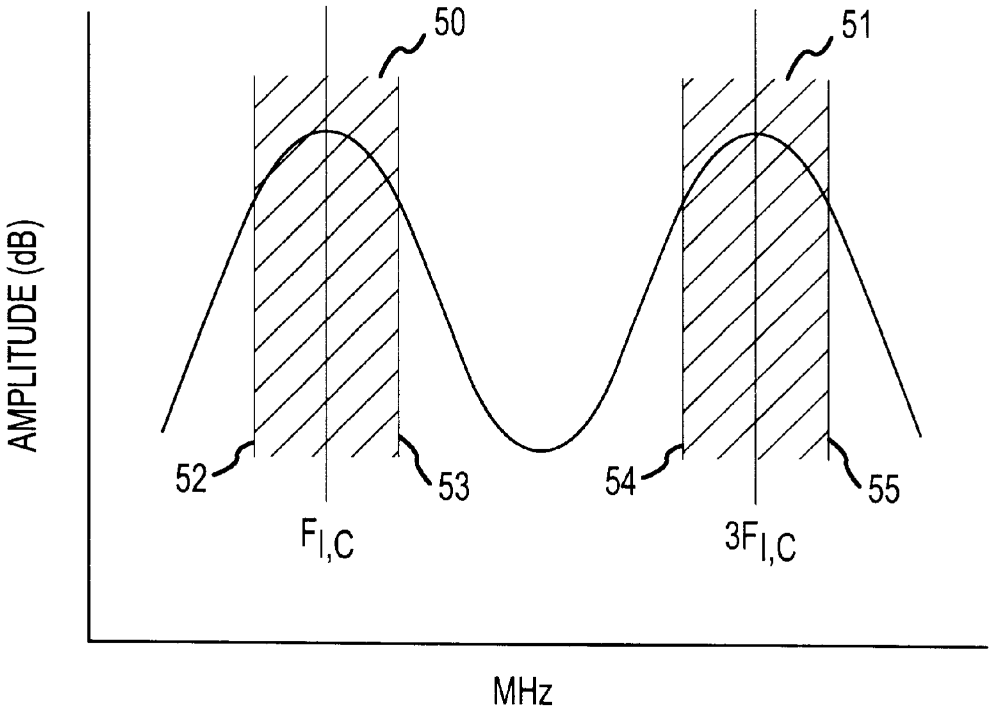
FIG. 3 is a graph illustrating a method of operation of an ultrasound imaging system according to another embodiment of the invention.

FIG. 3 is a graph that illustrates a method of operation of the ultrasound imaging system 10 of FIG. 1 according to another embodiment of the invention. As previously described, operation of the transducer assembly 30 of FIG. 1 in the $k_{31}$ mode produces resonances in the transducer 30 that are bimodal, so that frequencies confined within a first frequency band 50 will excite a fundamental resonant mode in the transducer assembly 30. In addition, the transducer assembly 30 will exhibit resonance at a third harmonic when excited by reflected waves at frequencies confined within a second frequency band 51. The first frequency band 50 accordingly includes a lower band frequency 52 and an upper band frequency 53. Similarly, the second frequency band 51 includes a lower band frequency 54 and an upper band frequency 55. The bandwidths of the first frequency band 50 and the second frequency band 51 are determined by the configuration of the filter networks 28 and 29, respectively.

In the present embodiment, the transmitter 21 is configured to transmit ultrasonic signals to the transducer assembly 30 that are approximately about a fundamental center frequency $f_{1,c}$, while the receiver is configured to receive ultrasonic signals that are approximately about a third harmonic center frequency $3f_{1,c}$. The system 10 is thus capable of performing harmonic imaging at approximately about the third harmonic frequency with enhanced sensitivity.

Since the transducer assembly 30 is capable of detecting reflected signals at approximately about the third harmonic frequency with greater sensitivity than is obtainable from conventional systems, the foregoing embodiment advantageously permits diagnostic imaging to be performed using third harmonic reflections from interior portions of a body. In contrast, conventional systems have generally employed transducer assemblies having extremely wide bandwidths, which still yield relatively low sensitivity to third harmonic reflections when compared to the present embodiment.

Figure 4:
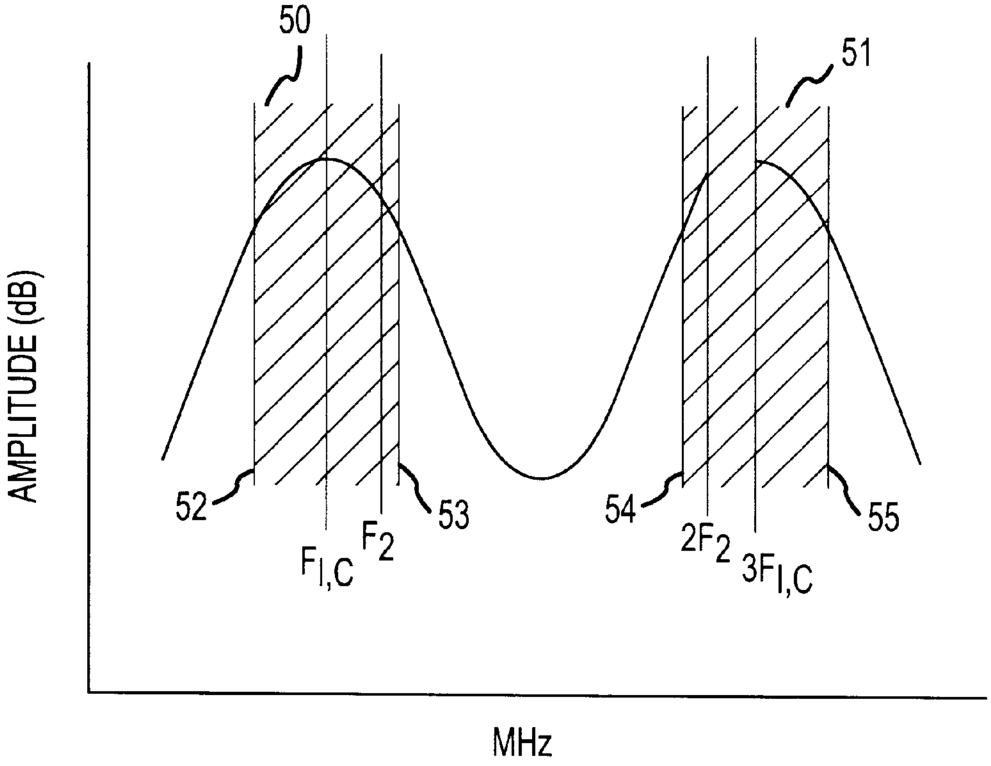
FIG. 4 is a graph illustrating a method of operation of an ultrasound imaging system according to still another embodiment of the invention.

FIG. 4 is a graph that illustrates another method of operation of the system 10 of FIG. 1 according to still another embodiment of the invention. Again, operation of the transducer assembly 30 of FIG. 1 in the $k_{31}$ mode produces bimodal resonance in the transducer 30, so that frequencies confined within the first frequency band 50 excite the fundamental resonant mode in the transducer assembly 30, and will exhibit resonance at a third harmonic when excited by reflected waves at frequencies confined within the second frequency band 51. In the present embodiment, the transmitter 21 is configured to transmit ultrasonic signals at approximately about a frequency $f_1$ that is close to the upper band frequency 53 of the first frequency band 50, while the receiver 22 is configured to receive signals at approximately a frequency $2f_1$ that is close to the lower band frequency 54 of the second frequency band 51, which approximately corresponds to a second harmonic resonant frequency of the transducer assembly 30. The system 10 is therefore capable of detecting signals at approximately about the second harmonic frequency for use in harmonic imaging.

The foregoing embodiment advantageously permits ultrasonic harmonic imaging to be performed where a second harmonic signal is the predominant reflected signal. In contrast to previous systems that employ transducer assemblies having a wide bandwidth, the present embodiment is expected to exhibit greater sensitivity to reflected signals at second harmonic frequencies. In contrast to other prior art systems that employ transducer assemblies having multiple piezoelectric layers and multiple electrode layers interposed between the layers (e.g. U.S. Pat. No. 5,957,851 to Hossack), the present embodiment is expected to exhibit favorable sensitivity to reflected waves at second harmonic frequencies without the use of additional layers and/or electrodes, thus generally reducing the complexity and cost of the imaging system.

The above description of illustrated embodiments of the invention is not intended to be exhaustive or to limit the invention to the precise form disclosed. While specific embodiments of, and examples of, the invention are described in the foregoing for illustrative purposes, various equivalent modifications are possible within the scope of the invention, as those skilled in the relevant art will recognize. Moreover, the various embodiments described above can be combined to provide further embodiments. Accordingly, the invention is not limited by the disclosure, but instead the scope of the invention is to be determined entirely by the following claims.

What is claimed is:

1. A system for harmonic imaging, comprising:

a transducer assembly configured for operation in a $k_{31}$ mode;

a transmitter for transmitting first signals to the transducer assembly, the first signals including a first frequency; and a receiver for processing second signals received by the transducer assembly, the second signals including a second frequency harmonically related to the first frequency.

2. The system according to claim 1, wherein the second frequency comprises a second harmonic frequency of the first frequency.

3. The system according to claim 2, wherein the transmitter is configured to transmit the first frequency at a frequency proximate to an upper band frequency of a first frequency band, and the receiver is configured to receive the second frequency at a frequency proximate to a lower band frequency of a second frequency band, wherein the second frequency band includes a frequency corresponding to the second harmonic frequency of the first frequency.

4. The system according to claim 1, wherein the second frequency comprises a third harmonic frequency of the first frequency.

5. The system according to claim 1, wherein the first frequency comprises a fundamental resonant frequency of the transducer assembly, and the transmitter is configured to transmit the first signals including a signal at the fundamental resonant frequency, and the second frequency comprises a third harmonic frequency, and the receiver is configured to receive the second signals including a signal at the third harmonic frequency.

6. The system according to claim 1, further comprising a first filter network coupled to the transmitter that is configured to confine the first signals to a first frequency band, the first band excluding frequencies harmonically related to the first frequency, and a second filter network coupled to the receiver that is configured to confine the second signals to a second frequency band that includes at least the second harmonic and third harmonic frequencies while excluding the first frequency, the first frequency band having an upper band frequency and the second frequency having a lower band frequency.

7. The imaging system according to claim 1, wherein the transducer assembly further comprises a piezoelectric layer having a first longitudinal dimension extending in a first direction and a second lateral dimension extending in a second direction, the ratio of the first dimension to the second dimension being at least about two.

8. The imaging system according to claim 1 wherein the transducer assembly further comprises a piezoelectric layer having a first longitudinal dimension extending in a first direction and a second lateral dimension extending in a second direction, the ratio of the first dimension to the second dimension being approximately three.

9. A method of operating an ultrasound imaging system, comprising:

emitting first ultrasound signals from a transducer assembly operating in a mode which is the $k_{31}$ mode, the first signals being confined to a first frequency range;

projecting the first ultrasound signals into a body; and detecting second ultrasound signals corresponding to reflected portions of the first signals, the second signals being confined to a second frequency range different from the first frequency range.

10. The method according to claim 9, wherein emitting first ultrasound signals further comprises emitting a signal corresponding to a first fundamental resonant frequency of the transducer assembly.

11. The method according to claim 9, wherein detecting second ultrasound signals further comprises detecting a signal corresponding to a third harmonic of the fundamental resonant frequency of the transducer assembly.

12. The method according to claim 9, wherein detecting second ultrasound signals further comprises detecting a signal corresponding to a second harmonic of the fundamental resonant frequency of the transducer assembly.

13. The method of claim 9, wherein emitting first ultrasound signals further comprises emitting signals that are proximate to an upper band frequency of the first frequency range, and further wherein detecting second ultrasound signals further comprises detecting signals that are proximate to a lower band frequency of the second frequency range.

14. An ultrasound imaging system, comprising:

a transducer assembly including at least one transducer element formed from a piezoelectric material extending in a first emitting direction and in a second direction that is perpendicular to the first direction and having electrodes positioned on opposing sides of the transducer element that intersect the second direction, the piezoelectric material being poled in the second direction; and an ultrasound processor operatively coupled to the electrodes, the processor transmitting first signals to the transducer assembly for generating ultrasonic waves, and receiving second signals from the transducer assembly corresponding to reflected portions of the ultrasonic waves, the second signals being harmonically related to the first signals.

15. The imaging system according to claim 14, wherein the first signals further include a fundamental resonant frequency of the transducer assembly, and the second signals include a frequency which is a second harmonic of the fundamental resonant frequency of the transducer assembly.

16. The imaging system according to claim 14, wherein the first signals further include a fundamental resonant frequency of the transducer assembly, and the second signals include a frequency which is a third harmonic of the fundamental resonant frequency of the transducer assembly.

17. The imaging system according to claim 14, wherein the first signals are confined to a first frequency band having an upper band frequency, and the second signals are confined to a second frequency band having a lower band frequency, and the processor is configured to transmit signals proximate to the upper band frequency, and to receive signals proximate to the lower band frequency, wherein the received signals include a frequency corresponding to the second harmonic frequency of the transducer assembly.

18. The imaging system according to claim 14, wherein the first signals are confined to a first frequency band, and the second signals are confined to a second frequency band, the first frequency band having a first center frequency and the second frequency band having a second center frequency, wherein the first center frequency is a fundamental resonant frequency of the transducer assembly and the processor is configured to transmit signals at about the fundamental resonant frequency, and the second center frequency is a third harmonic resonant frequency of the transducer assembly, and the processor is configured to receive signals at about the third harmonic resonant frequency.

19. The imaging system according to claim 14, further comprising a piezoelectric layer having a first dimension extending in the first direction and a second dimension extending in the second direction which exhibit a ratio therebetween, and wherein the ratio of the first dimension to the second dimension is at least two.

20. The imaging system according to claim 14, further comprising a piezoelectric layer having a first dimension extending in the first direction and a second dimension extending in the second direction which exhibit a ratio therebetween, and wherein the ratio of the first dimension to the second dimension is approximately about three.

* * * * *